(12) United States Patent
Acosta

(10) Patent No.: US 10,588,775 B2
(45) Date of Patent: Mar. 17, 2020

(54) MALE EXTERNAL CATHETER

(71) Applicant: Fred Acosta, Humble, TX (US)

(72) Inventor: Fred Acosta, Humble, TX (US)

(73) Assignee: Acosta Medical Group, Houston, TX (US)

( * ) Notice: Subject to any disclaimer, the term of this patent is extended or adjusted under 35 U.S.C. 154(b) by 0 days.

(21) Appl. No.: 14/995,672

(22) Filed: Jan. 14, 2016

(65) Prior Publication Data

US 2017/0216081 A1    Aug. 3, 2017

(51) Int. Cl.
| | | |
|---|---|---|
| *A61M 25/00* | (2006.01) | |
| *A61M 39/10* | (2006.01) | |
| *A61M 39/24* | (2006.01) | |
| *A61F 5/453* | (2006.01) | |

(52) U.S. Cl.
CPC ............. *A61F 5/453* (2013.01); *A61M 39/10* (2013.01); *A61M 39/24* (2013.01)

(58) Field of Classification Search
CPC ....... A61F 5/453; A61M 39/10; A61M 39/24; A61M 25/0017
See application file for complete search history.

(56) References Cited

U.S. PATENT DOCUMENTS

| | | | | | |
|---|---|---|---|---|---|
| 2,940,450 | A | * | 6/1960 | Witt ......................... | A61F 5/453 604/353 |
| 4,022,213 | A | * | 5/1977 | Stein ........................ | A61F 5/453 604/350 |
| 4,655,755 | A | * | 4/1987 | Ruffini .................... | A61F 5/453 604/352 |
| 4,713,067 | A | * | 12/1987 | Rothenberg ............ | A61F 5/453 24/30.5 R |
| 5,013,308 | A | * | 5/1991 | Sullivan .................. | A61F 5/453 604/349 |
| 5,261,708 | A | * | 11/1993 | Steer ....................... | A61F 5/448 285/319 |
| 5,318,550 | A | * | 6/1994 | Cermak .................. | A61F 5/453 604/349 |

(Continued)

*Primary Examiner* — Adam Marcetich
(74) *Attorney, Agent, or Firm* — Gregory L. Porter; James C. Wilson; Hunton Andrews Kurth LLP

(57) ABSTRACT

The external male catheter is designed to be attached to a drain tube of a standard catheter, with the catheter being non-invasive of the penis. The catheter includes a base secured to the pelvic area of a wearer, the base having a central opening for accommodating a penis. Connected to the base is a sheath for housing the penis, one end of the sheath adjacent the base and a second end of the sheath extending beyond the glans of the penis. The central opening and the sheath have complementary attachment components whereby the sheath may be attached to the base. The sheath includes an opening and attachment means for attaching the sheath to a drain tube. In the preferred embodiment of the invention a second sheath is disposed outboard of the first sheath and secured to the base in a similar manner. This protects the first sheath and penis from contamination. A coupler is provided between each sheath and the drain tube, whereby drain tube may be connected and disconnected from the sheath or sheaths without disturbing the installation of the catheter. It is desirable that the coupler for the drain tube includes a check valve assuring one-way flow in the drain tube.

17 Claims, 1 Drawing Sheet

(56) References Cited

U.S. PATENT DOCUMENTS

| | | | |
|---|---|---|---|
| 5,409,475 A * | 4/1995 | Steer | A61F 5/453 4/144.3 |
| 5,423,785 A * | 6/1995 | Hart | A61F 5/453 604/317 |
| 5,618,277 A * | 4/1997 | Goulter | A61F 5/4405 604/349 |
| 5,797,890 A * | 8/1998 | Goulter | A61F 5/453 604/351 |
| 6,248,096 B1 | 6/2001 | Dwork et al. | |
| 6,551,293 B1 | 4/2003 | Mitchell | |
| 6,635,037 B1 | 10/2003 | Bennett | |
| 6,679,867 B2 | 1/2004 | Miskie | |
| 7,066,918 B2 | 6/2006 | Bauhahn et al. | |
| 7,087,043 B2 | 8/2006 | Dolan | |
| 7,658,730 B2 | 2/2010 | Conley | |
| 9,101,490 B2 | 8/2015 | Mokrane | |
| 9,254,218 B2 | 2/2016 | Newton, Jr. | |
| 9,861,512 B2 | 1/2018 | Bourke | |
| 2002/0026163 A1 * | 2/2002 | Grundke | A61F 5/453 604/347 |
| 2004/0176746 A1 * | 9/2004 | Forral | A61F 5/453 604/544 |
| 2005/0283127 A1 * | 12/2005 | Miskie | A61F 5/453 604/349 |
| 2009/0259206 A1 * | 10/2009 | Kai | A61F 5/44 604/352 |
| 2012/0238976 A1 * | 9/2012 | Foster | A61F 5/4408 604/353 |
| 2013/0245586 A1 * | 9/2013 | Jha | A61F 5/443 604/352 |
| 2014/0121649 A1 * | 5/2014 | Calco | A61F 13/0206 604/543 |
| 2014/0350501 A1 * | 11/2014 | Garcia Calero | A61F 5/453 604/353 |
| 2015/0080818 A1 | 3/2015 | Sekiyama et al. | |
| 2015/0209647 A1 * | 7/2015 | MacFarland | A41D 13/0506 2/466 |
| 2017/0196726 A1 | 7/2017 | SanAntonio | |

* cited by examiner

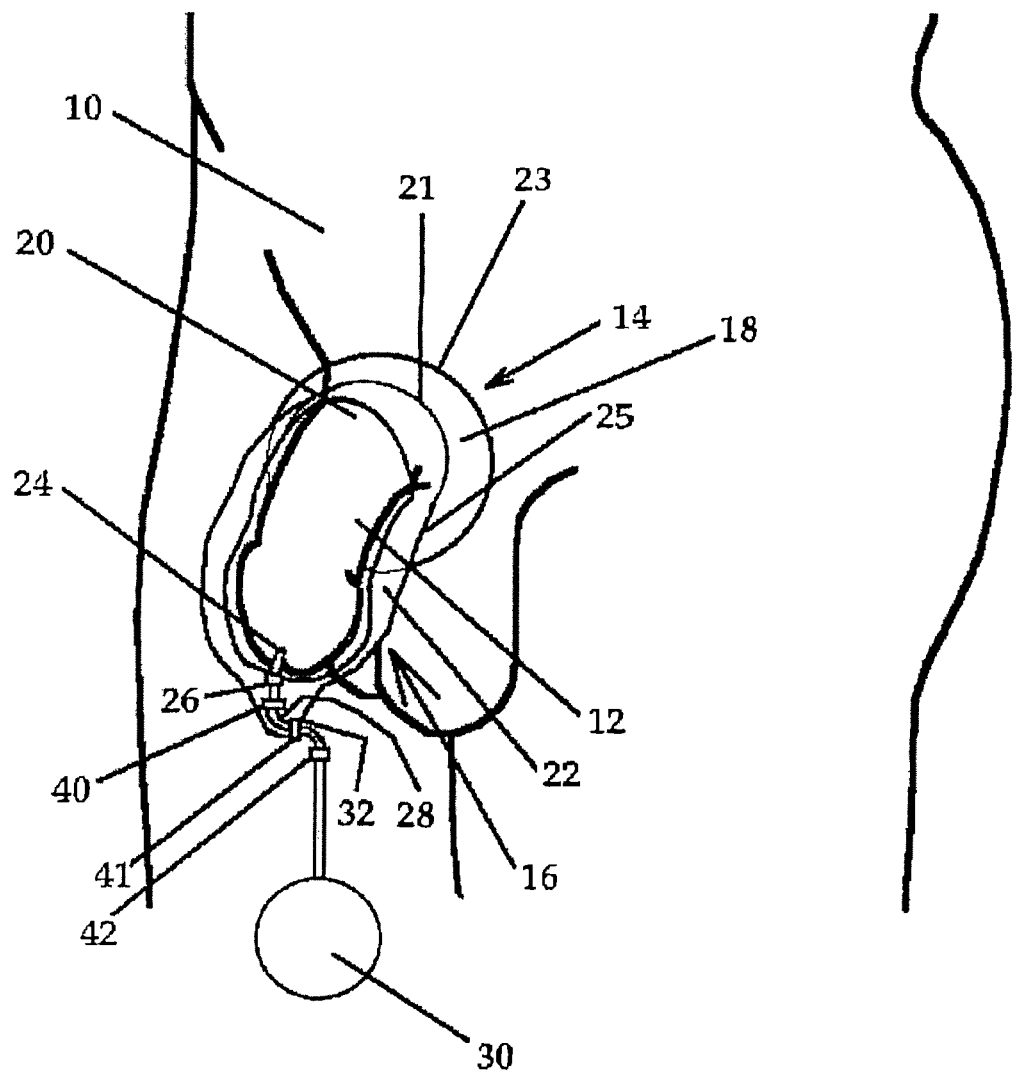

MALE EXTERNAL CATHETER

BACKGROUND OF THE INVENTION

Field of the Invention

This invention is related to urine collection devices and is specifically directed to male catheters.

Discussion of the Prior Art

Historically, external male urinary catheters were generally retained on a penis with an adhesive tape or similar pressure sensitive adhesive means, whereby the catheter could be readily attached by applying pressure to the adhesive bearing area of the catheter and securing it to the penis. Self-sealing catheters which do not require an adhesive have been more recently developed, as well. Both adhesive and self-sealing external catheters are difficult to apply, especially to males having a recessive penis.

The strapless catheters on the market have the adhesive sandwiched between successive rolls of the catheter. As the catheter is unrolled, the inner surface comes into contact with the penile surface ad is then pressed to seal. The sealing surface is generally located on the shaft, behind the glans.

A glans cap catheter is also available and is shaped like a cup to fit only over the glans. This has been generally unsuccessful because a glans-only seal does not withstand body movement and urine pressure unless an aggressive adhesive is used. This generally can cause pain and damage during removal.

A more recent condom catheter is shown in U.S. Pat. No. 5,334,175, issued on Aug. 2, 1994 to Conway, et al. This catheter includes a section which can conform to the shape of the penile tip and to adhere to it. The catheter can be unrolled onto and adhere to the penile shaft. The opposite end can be pulled into an elongated tube which serves as a urine collector.

Another example of a condom style catheter is shown and described in U.S. Pat. No. 4,626,250, issued on Dec. 2, 1986 to Schneider. This external catheter includes an adhesive element mounted on the shaft of the penis with the catheter being adhesively applied to the adhesive element by placing the catheter over the glans and then unrolling the adhesive portion onto the adhesive element.

All of the prior art devices have drawbacks in that they are hard to apply, especially with a recessive penis, can cause pain and injury when removed from the shaft, and have tendency to leak.

There remains a need for an external male catheter that is secure once applied, minimizes pain and injury to the penis, and is virtually leak proof.

SUMMARY OF THE INVENTION

The subject invention eliminates the shortcomings of the prior art external male catheters by moving the attachment element from the penis to the pelvic area and providing a tube which loosely envelopes the penis with a release tube extending form the penis tube and into a drain bag. The drain bag and/or release tube may be detachably connected to the penis tube with a clip or similar means. This permits the catheter to be emptied without removing any portion of the collection elements of the catheter.

The external male catheter of the subject invention is designed to be attached to a drain tube of a standard catheter, with the catheter being non-invasive of the penis. The catheter includes a base secured to the pelvic area of a wearer, the base having a central opening for accommodating a penis. Connected to the base is a sheath for housing the penis, one end of the sheath adjacent the base and a second end of the sheath extending beyond the glans of the penis. The central opening and the said one end of the sheath have complementary attachment components whereby the sheath may be attached to the base. The second end of sheath includes an opening and attachment means for attaching the sheath to a drain tube. In the preferred embodiment of the invention a second sheath is disposed outboard of the first sheath and secured to the base in a similar manner, the second sheath including an outer end with an opening through which the drain tube may be passed. This protects the first sheath and penis from contamination.

A coupler is provided between each sheath and the drain tube, whereby drain tube may be connected and disconnected from the sheath or sheaths without disturbing the installation of the catheter. The attachment means for the sheath to the base is selectively detachable, to accommodate examination and maintenance. One exemplary form of attachment is a Ziploc-type fastener. Another exemplary form of attachment is a Velcro-type fastener. It is desirable that the coupler for the drain tube includes a check valve assuring one-way flow in the drain tube.

The penile tube is connected directly to the body in the pelvic area with the tube extending therefrom to receive and house the penis. The penis is not interfered with in any manner and is simply "housed" in the penis tube. This minimizes discomfort for the user. The penis tube may be double sheathed to protect against contamination.

In certain applications, the external catheter of the subject invention may be used in combination with an in dwelling catheter which may be removed and replaced with the external release tube of the invention. This is particularly useful when an in dwelling catheter may be required immediately after surgery, for example, but could be removed after a short time even though the wearer remains incontinent. This permits long term use of a urine collector without exposing the penis to disease or infections such as sepsis, contrary to the issues common to in dwelling catheters.

In the preferred embodiment the external male catheter includes an adhesive base which has a central opening for permitting the penis to extend through the base. The base has an adhesive back, or may be made of a duoderm material which sticks to the skin. The base is attached directly to the skin in the pelvic area and completely surrounds the penis. The central opening includes a sealing edge, such as a Ziploc type seal, for receiving the connective end of the penis tube or sheath. This permits the penis to be housed in the tube and the tube to be connected to the base.

It is desirable that the penis be double sheathed to protect against infection or contamination. In this case, a second, generally concentric sealing edge is provided in the base for a second or outer sheath or tube.

At the outer end of each sheath is a release outlet for releasing urine from the penis tube. The release outlet may be connected to a standard type catheter tube by a clip or similar means. The catheter tube then drains into a collection bag. An advantage to the subject invention is the ability to remove the collection tube and bag from the penile sheath without disturbing the catheter installation.

The removable seal between the base and each sheath permits removal of the catheter from the penis without requiring reinstallation, greatly enhancing examination and hygiene management of the penile area.

BRIEF DESCRIPTION OF THE DRAWING

FIG. 1 is a diagrammatic view of the external catheter of the subject invention.

DETAILED DESCRIPTION OF AN EXEMPLARY EMBODIMENT

Referring generally to FIG. 1, the external male catheter of the subject invention is designed to be attached to a drain tube 28 of a standard catheter, with the catheter being non-invasive of the penis. The catheter includes a base 18 secured to the pelvic area 14 of a wearer, the base having a central opening 20 for accommodating a penis. Connected to the base is a sheath 22 for housing the penis, one end of the sheath adjacent the base 18 and a second end of the sheath extending beyond the glans of the penis. The central opening and the said one end of the sheath have complementary attachment components whereby the sheath may be attached to the base. The second end 24 of sheath includes an opening and attachment means for attaching the sheath to a drain tube 28. In the preferred embodiment of the invention a second sheath 25 is disposed outboard of the first sheath and secured to the base in a similar manner, the second sheath including an outer end 32 with an opening through which the drain tube may be passed. This protects the first sheath and penis from contamination.

One or more couplers 40, 41 and 42 are provided between each sheath and the drain tube, whereby drain tube may be connected and disconnected from the sheath or sheaths without disturbing the installation of the catheter. The attachment means for the sheath to the base is selectively detachable, to accommodate examination and maintenance. One exemplary form of attachment is a Ziploc-type fastener. Another exemplary form of attachment is a Velcro-type fastener. It is desirable that the coupler for the drain tube includes a check valve assuring one-way flow in the drain tube.

FIG. 1 is an illustration of the invention and shows a human body 10 with a penis 12 extending from the pelvic area 14. The subject invention is directed to an external male catheter 16 which is used with the penis 12. A base 18 includes a central hole or opening 20 large enough to permit the penis to pass freely through the base in a non-interfering manner. The back side of the base either is made of or includes an adhesive material that will attach the base directly to the skin of the wearer. A duoderm material is one suitable choice, but other adhesive devices may be employed as a matter of choice.

The central penis accommodating hole or opening 20 includes a rim 21 designed for attaching the penis sheath 22. The penis sheath loosely accommodates and encases the penis 12. The rim and end of the sheath have an attachment means such as a Velcro-type system of a Ziploc-type system for detachably securing the sheath to the base. The outer end 24 includes a release opening, such as a nipple 26 to which a catheter drain tube 28 may be attached either directly or through a series of couplers as will be described. The drain tub then empties the catheter into the collection bag 30, in the normal manner.

It is desirable to include a second sheath 25 outside the penis sheath 22 for sanitary purposes. The second sheath 25 is connected to the base by a connection element in a ring 23 outboard of the inn rim 21. In this application the outer tip 32 includes a release pro for accommodating the catheter discharge tube. The discharge tube is typically made of multiple sections with couplers 40, 41 and 42 to permit removal of bag 30 from the system without disturbing the penis encasing catheter. The couplers also facilitate installation and removal of each sheath for examination and maintenance purposes. The couplers may include one-way check valves to assure urine flow away from each sheath and the penis.

The external catheter of the invention provides a comfortable method and apparatus for applying an external catheter to a penis without leakage and with a minimum of discomfort and maintenance. While certain features and embodiments have been described in detail herein, it should be understood that the invention encompasses all modifications and enhancements within the scope and spirit of the following claims.

What is claimed is:

1. A collection device comprising:
a base designed to be secured to the pelvic area of a wearer, the base comprising a central opening wherein the central opening is large enough to allow a penis to pass freely through; and
a first sheath having a first end and a second end, wherein the first sheath is designed to loosely accommodate a penis, the first end of the first sheath designed to be in contact with and attached to the base around the central opening and the second end of the first sheath comprising an opening; and a second sheath, wherein the second sheath has a first end and a second end, the first end of the second sheath designed to be attached to the base around the central opening outboard of the first sheath and the second end of the second sheath comprising an opening designed to allow a separate drain tube to be passed through and for selectively attaching the second sheath to a separate drain tube.

2. The collection device of claim 1 further comprising a drain tube and a coupler, the coupler connecting the second sheath and the drain tube, the coupler configured such that the drain tube may be connected and disconnected from the second sheath without (1) detaching the second sheath from the base or (2) unsecuring the base from the pelvic area of the wearer or (3) both (1) and (2).

3. The collection device of claim 2 further comprising a check valve for one-way flow in the drain tube away from the pelvic area of the wearer.

4. The collection device of claim 2 further comprising a collection bag attached to the drain tube.

5. The collection device of claim 1, wherein the first end of the first sheath and the first end of the second sheath are designed to be selectively attachable to the base.

6. The collection device of claim 1 wherein the second end of the first sheath and second end of the second sheath comprise release outlets.

7. The collection device of claim 1, wherein the base comprises a rim designed for attaching the first sheath to the base.

8. The collection device of claim 1, wherein the first end of the first sheath is designed to be detachably attached to the base.

9. The collection device of claim 1, wherein the first end of the first sheath is designed to be selectively detachable to the base using a Ziploc-type fastener.

10. The collection device of claim 1, wherein the first end of the first sheath is designed to be selectively detachable to the base using a Velcro-type fastener.

11. The collection device of claim 1, wherein the base is designed to be adhesively secured to the pelvic area of a wearer.

12. The collection device of claim 1 wherein the central opening of the base is designed to accommodate a penis.

13. A collection device comprising:
a base designed to be secured to the pelvic area of a wearer, the base comprising a central opening wherein the central opening is large enough to allow a penis to pass freely through; and
a first sheath having a first end and a second end, wherein the first sheath is designed to loosely accommodate a penis, the first end of the first sheath designed to be in contact with and attached to the base around the central opening and the second end of the first sheath comprising an opening wherein first sheath is designed to extend beyond the glans of the penis and wherein the opening at the second end of the first sheath is designed to allow a separate drain tube to be passed through, wherein the separate drain tube may be selectively attached to the first sheath.

14. A male collection device comprising:
a base designed to be secured to the pelvic area of a wearer, the base comprising a central opening for accommodating a penis wherein the central opening is large enough to allow a penis to pass freely through; and
a first sheath configured for loosely housing a penis, the sheath having a first end and a second end, the first end of the first sheath designed to be in contact with and attached to the base around the central opening and the second end of the first sheath comprising an opening;
a separate check valve attached to the opening at the second end of the first sheath such that the opening allows fluid to move from the first sheath out through the check valve; and
a second sheath, wherein the second sheath has a first end and a second end, the first end of the second sheath designed to be attached to the base around the central opening outboard of the first sheath and the second end of the second sheath comprising an opening designed to allow a separate drain tube to be passed through and for selectively attaching the second sheath to a separate drain tube.

15. The male collection device of claim 14 wherein the first sheath is designed to extend beyond the glans of the penis and wherein the opening at the second end of the first sheath is designed to allow a separate drain tube to be passed through, wherein the separate drain tube may be selectively attached to the first sheath.

16. The male collection device of claim 14 further comprising a drain tube and a collection bag attached to the drain tube.

17. The male collection device of claim 16 further comprising a check valve for one-way flow in the drain tube away from the pelvic area of the wearer.

* * * * *